(12) United States Patent
He et al.

(10) Patent No.: US 12,230,772 B2
(45) Date of Patent: Feb. 18, 2025

(54) SHAREABLE BATTERY PACK, TROLLEY, POWER SUPPLY SYSTEM, AND PORTABLE ULTRASONIC SYSTEM

(71) Applicant: SHENZHEN MINDRAY BIO-MEDICAL ELECTRONICS CO., LTD., Guangdong (CN)

(72) Inventors: Xujin He, Shenzhen (CN); Rui Hu, Shenzhen (CN); Zewei Tan, Shenzhen (CN); Yuting Shao, Shenzhen (CN); Zhiwu Chen, Shenzhen (CN); Yanjiao Chen, Shenzhen (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 377 days.

(21) Appl. No.: 17/582,529

(22) Filed: Jan. 24, 2022

(65) Prior Publication Data
US 2022/0149448 A1    May 12, 2022

Related U.S. Application Data

(63) Continuation of application No. PCT/CN2019/097522, filed on Jul. 24, 2019.

(51) Int. Cl.
*H01M 10/46* (2006.01)
*A61B 8/00* (2006.01)
(Continued)

(52) U.S. Cl.
CPC .......... *H01M 10/46* (2013.01); *A61B 8/4405* (2013.01); *A61B 8/4427* (2013.01); *A61B 8/54* (2013.01);
(Continued)

(58) Field of Classification Search
CPC .... H01M 10/46; H01M 10/44; H01M 50/247; H01M 2220/30; H01M 50/256;
(Continued)

(56) References Cited

U.S. PATENT DOCUMENTS 6,695,777 B2 * 2/2004 Solomon ................ A61B 8/00
600/437
2009/0224611 A1 9/2009 Chen
(Continued)

FOREIGN PATENT DOCUMENTS

CN        1610523 A    4/2005
CN     102579139 A    7/2012
(Continued)

OTHER PUBLICATIONS

PCT International Preliminary Report on Patentability mailed Feb. 3, 2022, issued in related International Application No. PCT/CN2019/097522, with English translation (11 pages).
(Continued)

*Primary Examiner* — Sanjay Cattungal
(74) *Attorney, Agent, or Firm* — Sheppard Mullin Richter & Hampton LLP

(57) ABSTRACT

A shareable battery pack for a portable ultrasonic apparatus, a trolley, a power supply system, and a portable ultrasonic system. The trolley can be connected to the portable ultrasonic apparatus and/or the shareable battery pack to supply power so as to extend operation time. Alternatively, the trolley is used to support the portable ultrasonic apparatus and/or the shareable battery pack without supplying power to extend operation time. In an embodiment, the shareable battery pack can be removed from the trolley, and then be fixedly connected to the portable ultrasonic apparatus to form an integral unit and serve as an external battery for the portable ultrasonic apparatus. Such design enables the por-
(Continued)

table ultrasonic apparatus to have extended operation time without relying on the trolley and requires only one shareable battery pack in special situations, thereby enhancing convenience of use.

19 Claims, 12 Drawing Sheets

(51) Int. Cl.
  *A61B 50/10* (2016.01)
  *H01M 10/44* (2006.01)
  *H01M 50/247* (2021.01)
  *H02J 7/00* (2006.01)

(52) U.S. Cl.
  CPC ............... *A61B 8/56* (2013.01); *A61B 50/10* (2016.02); *H01M 10/44* (2013.01); *H01M 50/247* (2021.01); *H02J 7/0068* (2013.01); *H01M 2220/30* (2013.01)

(58) Field of Classification Search
  CPC ....... A61B 8/4405; A61B 8/4427; A61B 8/54; A61B 8/56; A61B 50/10; A61B 50/22; A61B 8/4411; H02J 7/0068; H02J 2310/23; H02J 7/342; H02J 7/0044; Y02E 60/10
  See application file for complete search history.

(56) References Cited

U.S. PATENT DOCUMENTS

| | | | |
|---|---|---|---|
| 2013/0330588 A1* | 12/2013 | Ahn | A61B 8/4427 600/443 |
| 2015/0366538 A1 | 12/2015 | McKenna | |

FOREIGN PATENT DOCUMENTS

| | | |
|---|---|---|
| CN | 204060225 U | 12/2014 |
| CN | 206792483 U | 12/2017 |
| CN | 208400983 U | 1/2019 |
| DE | 202018100738 U1 | 3/2018 |

OTHER PUBLICATIONS

First Search dated Jun. 12, 2023, issued in related Chinese Application No. 201980094155.7 (3 pages).
First Office Action dated Jun. 27, 2023, issued in related Chinese Application No. 201980094155.7, with English machine translation (37 pages).
Supplementary Search dated Jan. 24, 2024 issued in related Chinese Application No. 201980094155.7 (2 pages).
Second Office Action dated Jan. 30, 2024, issued in related Chinese Application No. 201980094155.7, with English machine translation (47 pages).
PCT International Search Report and the Written Opinion mailed Apr. 22, 2020, issued in related International Application No. PCT/CN2019/097522, with partial English translation (12 pages).

* cited by examiner

SHAREABLE BATTERY PACK, TROLLEY, POWER SUPPLY SYSTEM, AND PORTABLE ULTRASONIC SYSTEM

CROSS-REFERENCE TO RELATED APPLICATION

This is a continuation of International Patent Application No. PCT/CN2019/097522, filed with the China National Intellectual Property Administration (CNIPA) on Jul. 24, 2019. The entire content of the above-identified application is incorporated herein by reference.

TECHNICAL FIELD

The present disclosure relates to medical devices, in particular to devices for powering portable ultrasonic apparatus.

BACKGROUND

A portable ultrasonic apparatus inherently has a built-in battery. When the power consumption of the machine is certain, it can generally be achieved only by increasing the battery capacity to increase the battery life of the portable ultrasonic apparatus. The portable ultrasonic apparatus will thereby, however, be added in bulk and weight, which is not conducive to the flexibility of carrying and using the portable product.

Given that, a trolley is typically provided to the portable ultrasonic apparatus to increase its endurance. The trolley is usually provided with a built-in battery pack and a battery management circuit having functions of managing battery charge and discharge. The trolley charges the internal battery of the portable ultrasonic apparatus via an electrical interface of the trolley and that of the portable ultrasonic apparatus when they are coupled to each other, and also supplies power to the portable ultrasonic apparatus.

However, the battery life of the portable ultrasonic apparatus is heavily dependent on the trolley. In cases of no trolley in a hospital, or emergency visits without a trolley, portable ultrasonic apparatus cannot meet the needs of emergency visits and running for a long time due to their limited battery life.

SUMMARY

The present disclosure provides new shareable battery packs, trolleys, power supply systems and portable ultrasonic systems for portable ultrasonic apparatus to improve the convenience of current portable ultrasonic apparatus in terms of power supply.

A shareable battery pack provided in one embodiment may include:
 at least one battery for storing electrical energy;
 a housing having a holding cavity in which the at least one battery is accommodated, the housing comprising a first mounting part detachably coupled to the portable ultrasonic apparatus and a second mounting part detachably coupled to a trolley;
 a charging and discharging circuit electrically connected to the at least one battery and comprising a charging connector for charging the at least one battery and a discharging connector for discharging the at least one battery to charge the portable ultrasonic apparatus; and
 a control circuit for controlling the charging and discharging circuit to charge and discharge.

In one embodiment, the charging and discharging circuit may have a discharge equalization circuit and a charge equalization circuit to control the at least one battery to be discharged and charged.

In one embodiment, the housing may have a supporting member on which the portable ultrasonic apparatus can be placed.

In one embodiment, the supporting portion may have a supporting surface that matches the bottom of the portable ultrasonic apparatus.

In one embodiment, the supporting surface may have a convex or concave guiding portion for enabling the portable ultrasonic apparatus to move on the supporting surface along the guiding portions.

In one embodiment, it may further include a raised first limiting portion arranged in a direction in which the portable ultrasonic apparatus is inserted onto the shareable battery pack to limit the position of the portable ultrasonic apparatus with respect to the shareable battery pack.

In one embodiment, the housing may be flat, the supporting surface and the first mounting part may be arranged on the top wall of the housing, and the first mounting part and the first limiting portion may be arranged on opposite sides of the supporting surface respectively.

In an embodiment, the first mounting part may include a first snap-in connector protrudingly arranged on the housing for connecting with the portable ultrasonic apparatus in a buckled manner.

In one embodiment, the first mounting part may have two first snap-in connectors, a first unlocking member arranged between the two first snap-in connectors, first elastic members for driving the two first snap-in connectors to reset, and second elastic members for driving the first unlocking member to reset, wherein, the first elastic members may be respectively mounted in a line connecting the two first snap-in connectors and at opposite sides of the two first snap-in connectors, the first elastic members may be configured to drive the two first snap-in connectors to approach each other, and the first unlocking member may have a wide portion and a narrow portion, wherein the two first snap-in connectors may be pressed against both sides of the wide portion by the first elastic members, the second elastic members may be coupled to the first unlocking member to hold the wide portion of the first unlocking member between the two first snap-in connectors, the first unlocking member may protrude from the housing so that the position of the first unlocking member can be changed by a user to enable the two first snap-in connectors to abut on the narrow portion and change the distance between the two first snap-in connectors.

In an embodiment, the first snap-in connectors may protrude from the top wall of the housing, and the first unlocking member may protrude from the side wall of the housing.

In one embodiment, it may further include at least one first magnetic socket provided with a first magnetic member for conveniently attracting the portable ultrasonic apparatus and/or the trolley, wherein the charging connector and the discharging connector are arranged in the same or different first magnetic sockets so as to power the portable ultrasonic apparatus and charge the at least one battery.

In an embodiment, the second mounting part may include a bayonet arranged on the side of the housing, and the bayonet can be suitable to be fixed to a snap-in structure of the trolley.

In one embodiment, the shareable battery pack may include: a battery for storing electrical energy, a first mounting part detachably coupled to the portable ultrasonic apparatus, a second mounting part detachably coupled to a trolley, a charging and discharging circuit electrically connected to the battery, and a control circuit controlling the charging and discharging circuit to charge the battery and supply power to the portable ultrasonic apparatus.

A trolley provided in one embodiment may include:

a base; and a support table mounted on the base for supporting the shareable battery pack, wherein the support table has an installation part for bearing the shareable battery pack and a third mounting part detachably coupled to the shareable battery pack and/or the portable ultrasonic apparatus.

In one embodiment, it may further include a power supply having an output connector for docking with the shareable battery pack or portable ultrasonic apparatus, and a control circuit connected with the power supply for controlling the power supply to supply power to the shareable battery pack or to supply power to the portable ultrasonic apparatus.

In one embodiment, it may further include a charging wire having an electrical input terminal and an electrical output terminal, wherein the electrical output terminal is configured to electrically coupled to an external charging device, and the electrical input terminal is configured to dock with the shareable battery pack or the portable ultrasonic apparatus so as the current of the external charging device is conducted to the shareable battery pack or the portable ultrasonic apparatus.

In one embodiment, it may further include a power supply circuit for docking the shareable battery pack or portable ultrasonic apparatus with an external charging device, and controlling the external charging device to supply power to the shareable battery pack and/or the portable ultrasonic apparatus.

In one embodiment, the installation part may be on the top wall of the support table to enable the shareable battery pack to be detachably mounted on the top wall of the support table.

In one embodiment, the installation part may have a recessed installation cavity having an open at least at the top to place the shareable battery pack.

In one embodiment, at least one side wall of the installation cavity may be inclined in an outside-in manner, so that the shareable battery pack can slide into the installation cavity along the side wall.

In one embodiment, the installation cavity may be provided inside with a raised second limiting portion arranged in a direction in which the portable ultrasonic apparatus is inserted onto the shareable battery pack to limit the position of the shareable battery pack with respect to the shareable battery pack.

In one embodiment, the third mounting part may have a second snap-in connector for buckling the shareable battery pack.

In an embodiment, the third mounting part may further have a third elastic member and a second unlocking member that reset the second snap-in connector, wherein the third elastic member may actuate the second snap-in connector to protrude from the outer wall of the support table, and the second unlocking member may be in transmission connection with the second snap-in connector to move the second snap-in connector into the support table by means of the second unlocking member.

In one embodiment, the installation part may have a recessed installation cavity having at least one side wall inclined in an outside-in manner, and the second snap-in connector may be arranged on the inclined side wall and have a first hook portion for buckling the shareable battery pack, wherein the top wall of the first hook portion may be inclined downward to form a first guide surface to guide the shareable battery pack downwardly into the installation cavity.

In one embodiment, the second snap-in connector may be rotatably mounted in the support table, the second unlocking member may vertically abut against one end of the second snap-in connector, and a fourth elastic member may be arranged on the second unlocking member for resetting the second unlocking member upward.

In one embodiment, the second snap-in connector may have a first hook portion for buckling the shareable battery pack and a second hook portion arranged above the first hook portion for buckling the portable ultrasonic apparatus.

In one embodiment, the third mounting part further may have a third snap-in connector for buckling the portable ultrasonic apparatus.

In an embodiment, the third mounting part further may have a fifth elastic member and a third unlocking member that reset the third snap-in connector, the fifth elastic member may actuate the third snap-in connector to protrude from the outer wall of the support table, and the third unlocking member may be connected to the third snap-in connector as an integral or in a transmission connection so that the third snap-in connector is moved into the support table by means of the third unlocking member.

In one embodiment, the third snap-in connector may be arranged on a path the second snap-in connector is retracted, so that when the second snap-in connector is unlocked, it may drive the third snap-in connector to move towards the unlocking direction together.

In one embodiment, the installation part may have a recessed installation cavity, the third snap-in connector may be slidably arranged in the support table, the third unlocking member may be exposed outside the support table and be in transmission connection with the third snap-in connector, and the fifth elastic member may act on the third snap-in connector to drive the third snap-in connector to reset to a location protruding from the side wall of the installation cavity.

In an embodiment, when the shareable battery pack and the portable ultrasonic apparatus are installed on the trolley, the second snap-in connector in a locked position can drive the first mounting part of the shareable battery pack to turn into an unlocked position so as to enable the shareable battery pack and the portable ultrasonic apparatus to be in an unlocked state.

In one embodiment, it may further include at least one second magnetic socket provided with a second magnetic member for conveniently attracting the portable ultrasonic apparatus and/or the shareable battery pack, wherein the output connector may be arranged in the second magnetic socket for charging the portable ultrasonic apparatus and/or the shareable battery pack.

A power supply system for a portable ultrasonic apparatus provided in one embodiment may include:

a trolley; and a shareable battery pack configured to supply power to the portable ultrasonic apparatus and provided with a first mounting part detachably coupled to the portable ultrasonic apparatus and a second mounting part detachably coupled to the trolley; and the trolley is configured to charge the shareable battery pack and/or the portable ultrasonic apparatus, and is provided with a third mounting part detachably coupled to the shareable battery pack and/or the portable ultrasonic apparatus.

In one embodiment, the shareable battery pack described in the foregoing embodiments may be adopted.

In one embodiment, the trolley described in the above embodiments may be adopted.

A portable ultrasonic system provided in one embodiment may include:

a portable ultrasonic apparatus for ultrasonic examination;

a shareable battery pack detachably fixed to the portable ultrasonic apparatus and configured to supply power to it; and a trolley, on which the portable ultrasonic apparatus and the shareable battery pack are detachably mounted.

In one embodiment, the shareable battery pack described in the foregoing embodiments may be adopted.

In one embodiment, the trolley described in the foregoing embodiments may be adopted.

A trolley provided in one embodiment may include:

a base;

a support table mounted on the base; and a locking arrangement mounted on the support table and provided with a second snap-in connector, a third elastic member and a second unlocking member, wherein the second snap-in connector has at least a first hook portion for buckling a first member and a second hook portion arranged above the first hook portion for buckling a second member, the third elastic member has a first end abutted on the support table and a second end abutted on an end of the second snap-in connector away from the first and second hook portions and actuates the second snap-in connector to be in a locked state, and the second snap-in connector is in transmission connection with the second unlocking member and is in an unlocked state by means of the second unlocking member.

In one embodiment, it may further include a rotating shaft, wherein the second snap-in connector is rotatably connected to the support table with the rotating shaft as an axle center.

In one embodiment, the second unlocking member may vertically abut an end of the second snap-in connector away from the first and second hook portions and be provided with a fourth elastic member for resetting the second unlocking member upward.

A locking arrangement provided in one embodiment may include a second snap-in connector provided with at least a first hook portion for buckling a first member and a second hook portion arranged above the first hook portion for buckling the second member.

A trolley provided in one embodiment may include:

a base;

a support table mounted on the base; and a locking arrangement mounted on the support table and provided with at least a second snap-in connector, a third snap-in connector, a third elastic member and a second unlocking member, wherein the second snap-in connector has a first hook portion for buckling a first member, a third snap-in connector has a second hook portion for buckling a second member, the third elastic member has an end abutted against the side wall of the support table and another end abutted against one end of the second snap-in connector away from the first hook portion and actuates the second snap-in connector to be in a locked state, the second snap-in connector is in transmission with the second unlocking member and is in an unlocked state by means of the second unlocking member, and the third snap-in connector is arranged on a path the second snap-in connector is retracted so that when the second snap-in connector is unlocked, it drives the third snap-in connector to move towards the unlocking direction together.

In one embodiment, the locking arrangement may further include a fifth elastic member and a third unlocking member that reset the third snap-in connector, the fifth elastic member may have an end abutted against the side wall of the support table and another end abutted against the third unlocking member and may actuate the third snap-in connector to be in the locked state, and the third unlocking member may be connected to the third snap-in connector as an integral or in a transmission connection so that the third snap-in connector is in the unlocked state by means of the third unlocking member.

A locking arrangement provided in one embodiment may include at least a second snap-in connector, a third snap-in connector, a third elastic member and a second unlocking member, wherein the third elastic member may drive the second snap-in connector to be in the locked state, the second snap-in connector may be in transmission connection with the second unlocking member and be in the unlocked state by means of the second unlocking member, and the third snap-in connector may be arranged on a path the second snap-in connector is retracted so that when the second snap-in connector is unlocked, it may drive the third snap-in connector to move towards the unlocking direction together.

The present disclosure may provide a portable ultrasonic system and a power supply system thereof. In the power supply system and the portable ultrasonic system, the trolley and the shareable battery pack are in a detachable and combinable structure. The portable ultrasonic apparatus and the shareable battery pack can be fixedly installed on the trolley. The trolley can be connected to the portable ultrasonic apparatus and/or the shareable battery pack to supply power so as to extend operation time. Alternatively, the trolley is only used to support the portable ultrasonic apparatus and/or the shareable battery pack without supplying power to extend operation time. In special situations, the shareable battery pack can be removed from the trolley, and then be fixedly connected to the portable ultrasonic apparatus to form an integral unit and serve as an external battery for the portable ultrasonic apparatus. Such design enables the portable ultrasonic apparatus to have extended operation time without relying on the trolley and requires only one shareable battery pack in special situations, thereby enhancing convenience of use.

DETAILED DESCRIPTION

Figure 1:
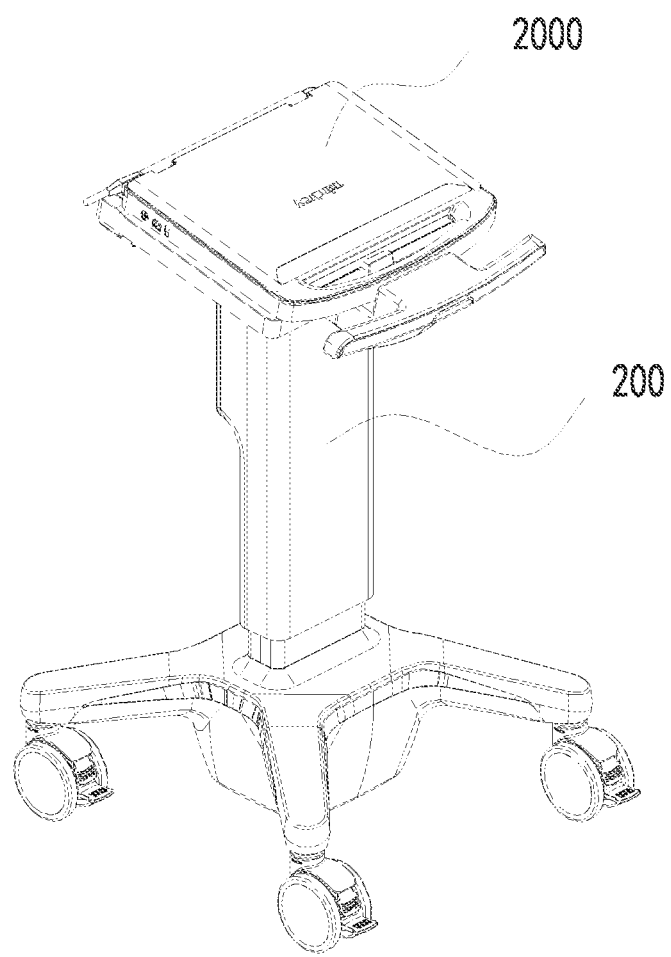
FIG. 1 schematically illustrates the structure of a portable ultrasonic system in an embodiment according to the present disclosure.

The present disclosure will be further described in detail below through specific embodiments with reference to the accompanying drawings. Common or similar elements are referenced with like or identical reference numerals in different embodiments. Many details described in the following embodiments are for better understanding the present disclosure. However, those skilled in the art can realize with minimal effort that some of these features can be omitted in different cases or be replaced by other elements, materials and methods. For clarity some operations related to the present disclosure are not shown or illustrated herein so as to prevent the core from being overwhelmed by excessive descriptions. For those skilled in the art, such operations are not necessary to be explained in detail, and they can fully understand the related operations according to the description in the specification and the general technical knowledge in the art.

In addition, the features, operations or characteristics described in the specification may be combined in any suitable manner to form various embodiments. At the same time, the steps or actions in the described method can also be sequentially changed or adjusted in a manner that can be apparent to those skilled in the art. Therefore, the various sequences in the specification and the drawings are only for the purpose of describing a particular embodiment, and are not intended to be an order of necessity, unless otherwise stated one of the sequences must be followed.

The serial numbers of components herein, such as "first", "second", etc., are only used to distinguish the described objects and do not have any order or technical meaning. The terms "connected", "coupled" and the like here include direct and indirect connections (coupling) unless otherwise specified.

Figure 2:
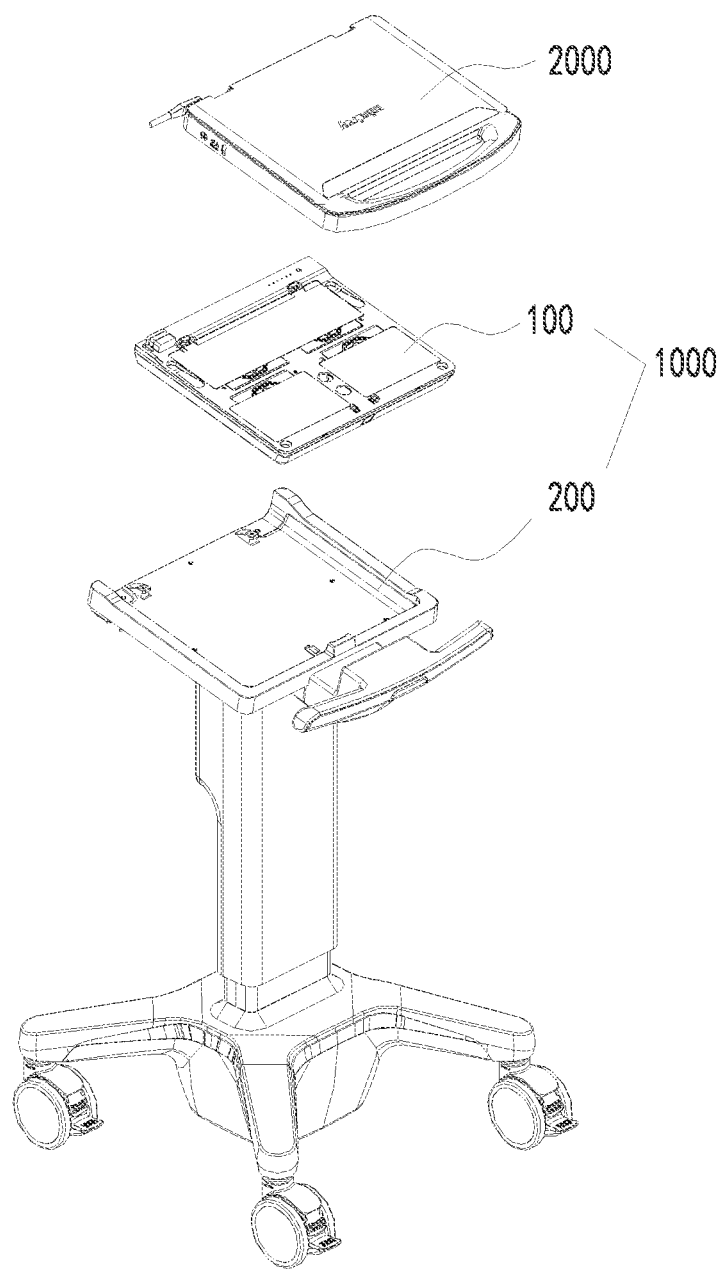
FIG. 2 schematically illustrates various parts of a portable ultrasonic system in an embodiment according to the present disclosure.
Figure 3:
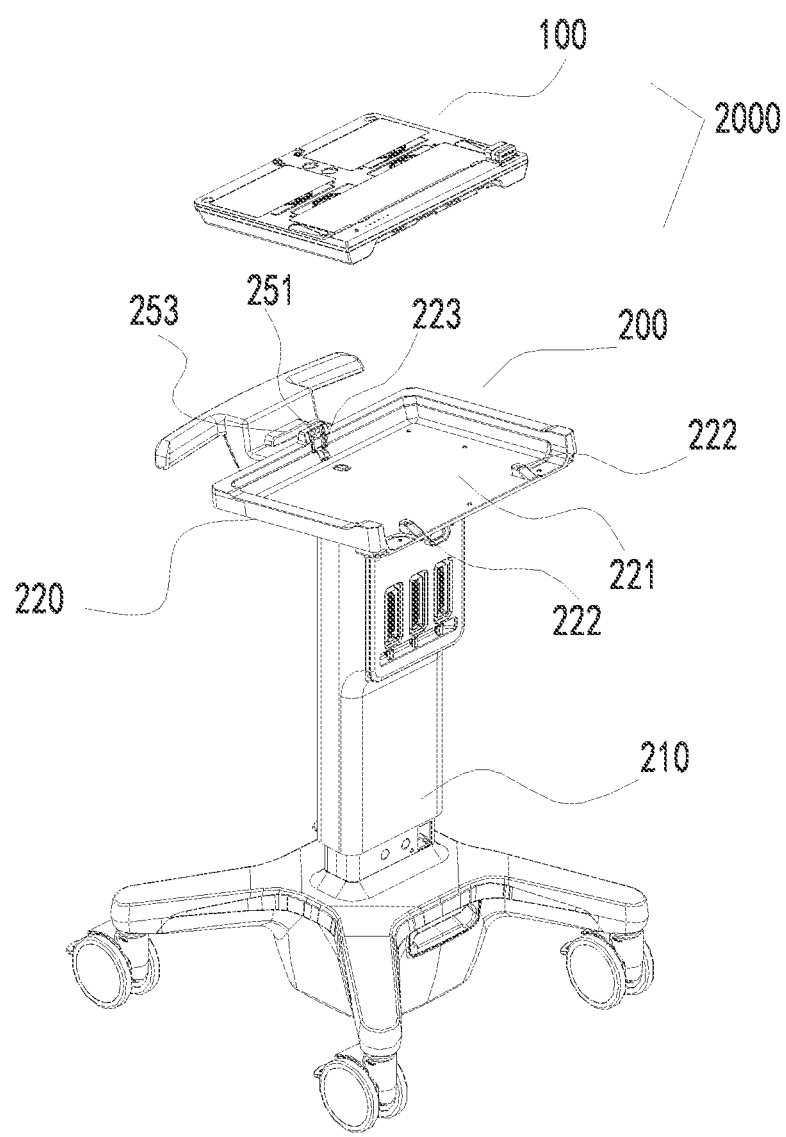
FIG. 3 schematically illustrates various parts of a power supply system in an embodiment according to the present disclosure.

Refer to FIGS. 1 to 3, a portable ultrasonic system provided in an embodiment according to the present disclosure may include a portable ultrasonic apparatus 2000 and a power supply system 1000 thereof.

The portable ultrasonic apparatus 2000 may be a variety of small ultrasonic devices that are easy to carry, such as a notebook ultrasonic device. A user can carry the portable ultrasonic apparatus 2000 for ultrasonic examination, thereby enhancing the convenience of using the ultrasonic device.

The power supply system 1000 may include a shareable battery pack 100 and a trolley 200. The shareable battery pack 100 can be detachably fixed with the portable ultrasonic apparatus 2000 to power the portable ultrasonic apparatus 2000. The portable ultrasonic apparatus 2000 and the shareable battery pack 100 may be detachably installed on the trolley 200. The user can remove the portable ultrasonic apparatus 2000 or the shareable battery pack 100 as needed.

In an embodiment, the shareable battery pack 100 may have a first mounting part, through which the first mounting part can be detachably connected to the portable ultrasonic apparatus 2000 as a whole. The first mounting part may adopt various structures of detachable fixed connection, such as a snap-fit structure, a threaded locking structure, an interference fit structure, a magnetic attraction structure, an adhesive structure and so on.

In some embodiments, the shareable battery pack 100 may also be detachably connected to the trolley 200. Accordingly, a second mounting part may be provided on the housing of the battery pack so that they can be detachably connected to the trolley 200 as a whole. Similarly, the second mounting part may adopt various structures of detachable fixed connection, such as a snap-fit structure, a threaded locking structure, an interference fit structure, a magnetic attraction structure, an adhesive structure, etc. Please refer to FIG. 5, in an embodiment, the second mounting part may include an unlocking opening 129 arranged on the side of the housing 120, and the unlocking opening 129 can be fixed to the snap-in structure of the trolley 200.

Of course, in some embodiments, the shareable battery pack 100 may not be fixed to the trolley 200, but to be fixed via the fixation of the portable ultrasonic apparatus 2000 and the trolley 200.

The trolley 200, configured to charge the shareable battery pack 100 and/or the portable ultrasonic apparatus 2000, may have a third mounting part so that they can be as a whole to detachably connect with the shareable battery pack 100 and/or the portable ultrasonic apparatus 2000. Similarly, the third mounting part may also adopt various structures of detachable fixed connection, such as a snap-fit structure, a threaded locking structure, an interference fit structure, a magnetic attraction structure, an adhesive structure and so on.

The shareable battery pack 100 can be fixedly installed on the trolley 200, electrically connected to the trolley 200, and used as a built-in battery of the trolley 200. The trolley 200 can be connected to the portable ultrasonic apparatus 2000 and/or the shareable battery pack 100 via an output connector to supply power so as to extend operation time. Alternatively, the trolley 200 may only be used to support the portable ultrasonic apparatus 2000 and/or the shareable battery pack 100 without supplying power to prolong operation time. In special situations, such as when it is inconvenient to use the trolley 200 for power supply, the shareable battery pack 100 can be removed from the trolley 200 and then be fixedly connected to the portable ultrasonic apparatus 2000 to form an integral unit and serve as an external battery for the portable ultrasonic apparatus 2000. Such design enables the portable ultrasonic apparatus 2000 to have extended operation time without relying on the trolley 200 and requires only one shareable battery pack in special situations, thereby enhancing convenience of use.

In one embodiment, the shareable battery pack 100 may include a battery for storing electric energy, a first mounting part that can be detachably connected to the portable ultrasonic apparatus 2000, a second mounting part that can be detachably connected to the trolley 200, a charging and discharging circuit and a control circuit. The charging and discharging circuit may be electrically connected to the battery, and the control circuit may control the charging and discharging circuit to charge the battery and supply power to the portable ultrasonic apparatus 2000.

Figure 4:
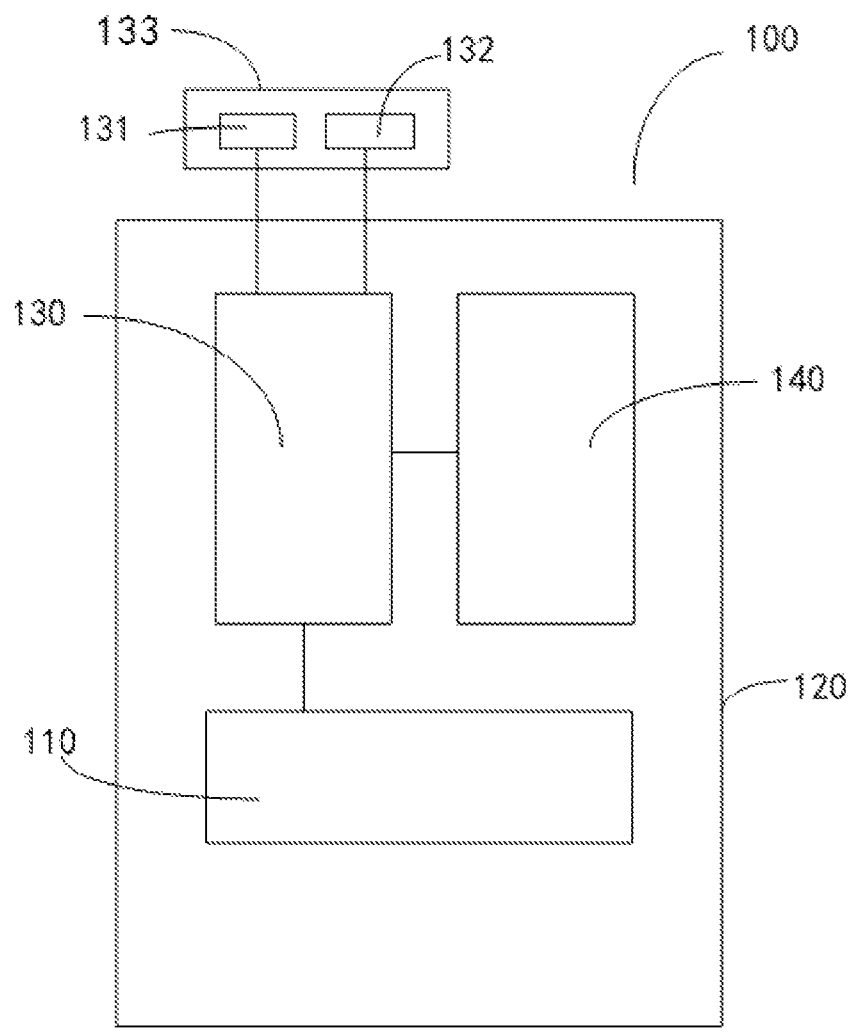
FIG. 4 is a block diagram that illustrates the circuit structure of a shareable battery pack in an embodiment according to the present disclosure.
Figure 5:
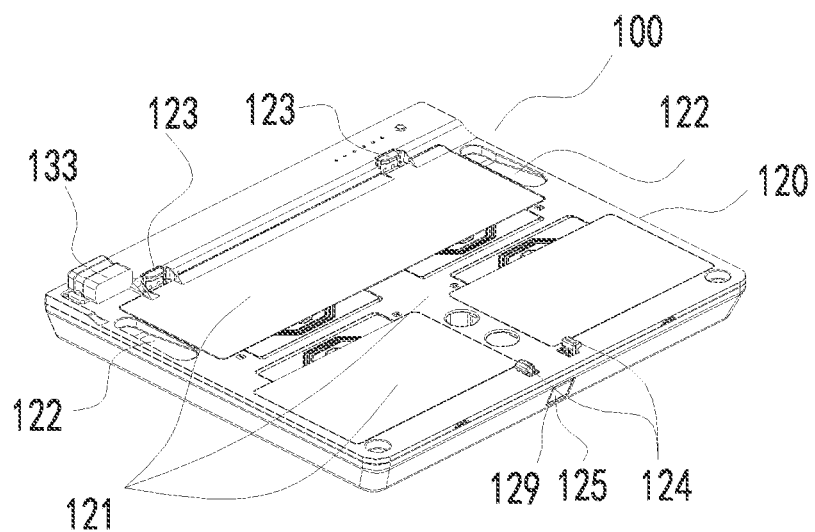
FIG. 5 schematically illustrates the appearance of a shareable battery pack in an embodiment according to the present disclosure.
Figure 6:
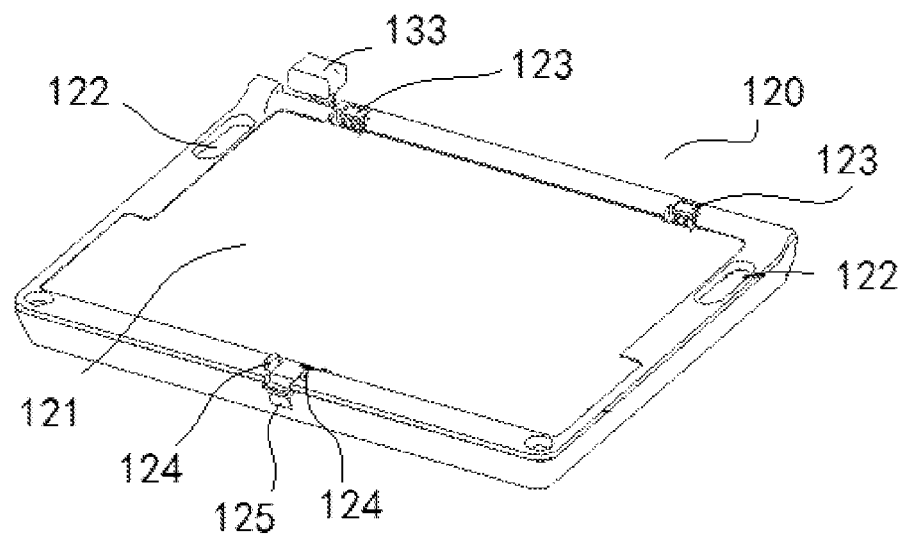
FIG. 6 schematically illustrates the appearance of a shareable battery pack in another embodiment according to the present disclosure.

Referring to FIGS. 4 to 6, in an embodiment, the shareable battery pack 100 may include at least one battery 110, a housing 120, a charging and discharging circuit 130 and a control circuit 140.

The battery 110 is used to store electrical energy. There may be more than one battery, which can be specifically selected according to actual charging requirements. The housing 120 may have a holding cavity, in which the battery 110 is installed. The housing 120 may be provided with a first mounting part detachably connected with the portable ultrasonic apparatus 2000.

The charging and discharging circuit 130, electrically connected to the battery 110, may have a charging connector 131 and a discharging connector 132. The charging connector 131 and the discharging connector 132 may be different or the same. The charging connector 131 can be electrically coupled to the trolley 200 or the adapter of the portable ultrasonic apparatus to charge the battery 110 of the shareable battery pack 100. The discharge connector 132 may be electrically coupled to and supply power to the portable ultrasonic apparatus 2000.

Please refer to FIG. 4, the control circuit 140 (e.g. MCU and peripheral circuits) may be electrically connected to the charging and discharging circuit 130 to control its charging and discharging. In some embodiments, the shareable battery pack 100 may also include some other conventional structures, such as an interface and current detection unit, a button and battery indicator unit, etc., which are not described in detail here.

Further, in an embodiment, the charging and discharging circuit 130 may have a discharge equalization circuit and a charge equalization circuit, so that each battery 110 can be discharged and charged in a balanced manner.

Further, in an embodiment, the housing 120 may have a supporting member, so that the portable ultrasonic apparatus 2000 can be placed on the supporting member. The shareable battery pack 100 may provide a stable support for the portable ultrasonic apparatus 2000 with the supporting member. The supporting member may be various supporting structures such as supporting surfaces of different shapes or brackets.

Figure 7:
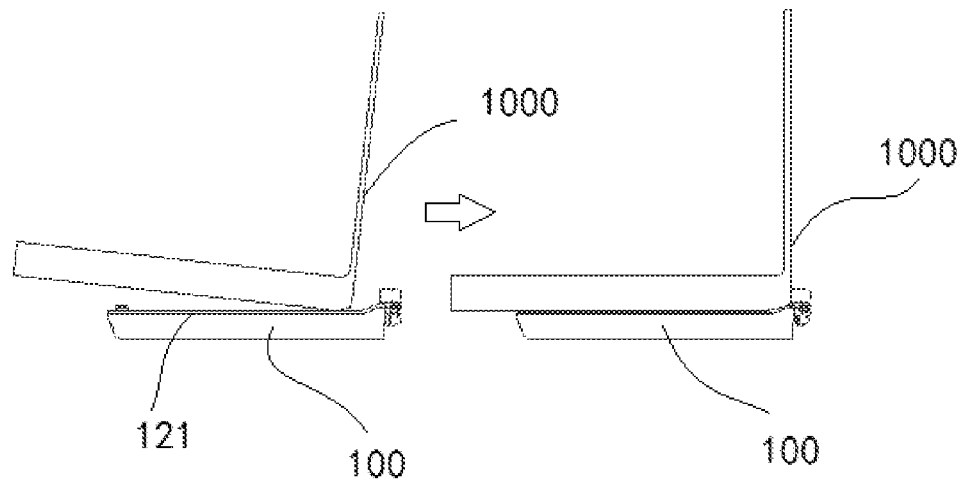
FIG. 7 schematically illustrates a process of installing a portable ultrasonic apparatus into a shareable battery pack in an embodiment according to the present disclosure.

Please refer to FIGS. 5 and 6, in an embodiment, the supporting member may have a supporting surface 121 that matches the bottom of the portable ultrasonic apparatus 2000. That is, the portable ultrasonic apparatus 2000 is installed above the shareable battery pack 100 so as not to be affected in its use by the latter shareable battery pack. As shown in FIG. 7, the portable ultrasonic apparatus 2000 may be placed upon the supporting surface 121 from the supporting surface 121 when in use. The design of the supporting surface 121 can simplify the structure of the shareable battery pack 100, without providing complicated supporting member. Also, its support can increase the contact area between the shareable battery pack 100 and the portable ultrasonic apparatus 2000, thereby ensuring the stability of the support.

Please refer to FIG. 6, the supporting surface 121 may be a flat structure integrally arranged on the top wall of the housing 120. Alternatively, referring to FIG. 5, the supporting surface 121 may also be a combination of a plurality of components mounted on the top wall of the housing 120, and the top wall of these components and the top wall of the housing 120 support together under the shareable battery pack 100.

Further, referring to FIGS. 5 and 6, in an embodiment, the supporting surface 121 may have a convex or concave guide portion 122 for moving the portable ultrasonic apparatus 2000 on the supporting surface 121 along the guide portion 122. As shown in FIGS. 5 and 6, the guide portion 122 may be a guide groove. In other embodiments, the guide portion 122 may be a guide rail or the like. The guide portion 122 may be arranged along the insertion direction of the portable ultrasonic apparatus 2000 so as to guide the portable ultrasonic apparatus 2000 to move smoothly to a right position.

Still referring to FIGS. 5 and 6, in an embodiment, the supporting surface 121 may have a convex first limiting portion 123 arranged in the insertion direction of the portable ultrasonic apparatus 2000 to define the position of the portable ultrasonic apparatus 2000. The first limiting portion 123 may, such as, be a bump, a barb, or a rib. There may be more than one first limiting portion 123 so that it or they may limit the portable ultrasonic apparatus 2000 from one or more positions.

Yet still referring to FIGS. 5 and 6, in an embodiment, the housing 120 may be flat, and the supporting surface 121 and the first mounting part may be on the top wall of the housing 120, so that the portable ultrasonic apparatus 2000 can be conveniently placed on the supporting surface 121. The first mounting part (such as a first snap-in connector 124) and the first limiting portion 123 may be respectively arranged on both sides of the supporting surface 121, so that the shareable battery pack 100 can position the portable ultrasonic apparatus 2000 from both ends. The flat housing may be, but not limited to, polygonal, circular, and special-shaped in shape.

Further, the first mounting part may be mainly used to detachably fix the portable ultrasonic apparatus 2000 and the shareable battery pack 100, so as to ensure that they can be integrated into an integrated structure, which is convenient to carry. Please refer to FIGS. 5, 6 and 8, in an embodiment, the first mounting portion may include a first snap-in connector 124 protruded and arranged on the housing 120 for engaging with the portable ultrasonic apparatus 2000. The first snap-in connector 124 may have a hook 1241 for buckling a corresponding structure on the portable ultrasonic apparatus 2000. The corresponding structure on the portable ultrasonic apparatus 2000 may also be a snap-in structure, or a bayonet or a buckling seat that can be fastened by the first snap-in connector 124.

Of course, conversely, a snap-in structure similar to the first snap-in connector 124 may also be arranged on the portable ultrasonic apparatus 2000 to buckle the first mounting part of the shareable battery pack 100. In this way, the first mounting part may be a bayonet, a buckling seat or other structures.

Figure 8:
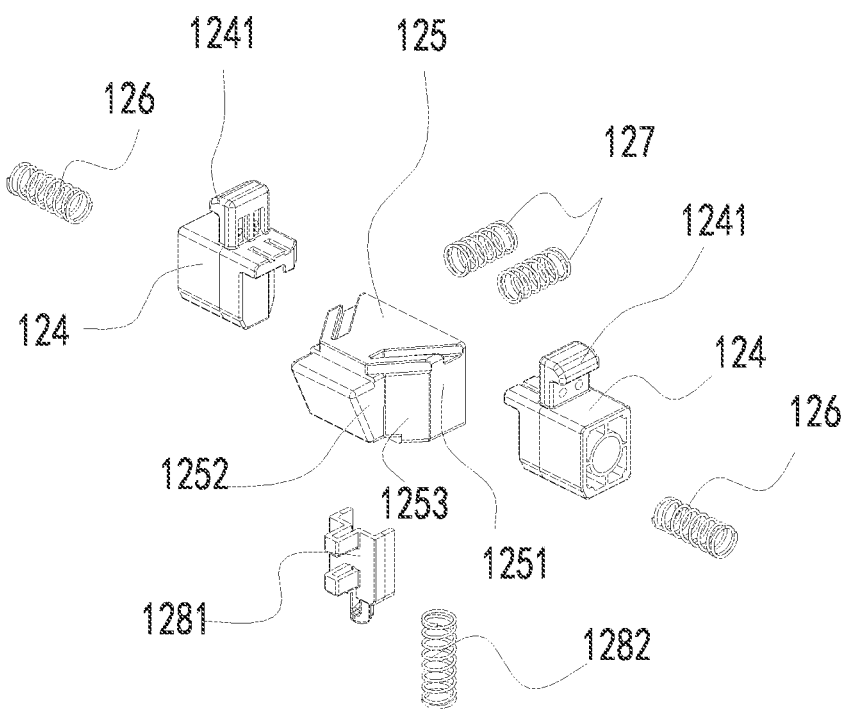
FIG. 8 is an exploded diagram that schematically illustrates the components of a first mounting part on a shareable battery pack in an embodiment according to the present disclosure.

Refer to FIGS. 5, 6 and 8, in an embodiment, the first mounting part may have two first snap-in connectors 124 arranged opposite to each other, a first unlocking member 125 arranged between the two first snap-in connectors 124, a first elastic member 126 driving the first snap-in connector 124 to be reset, and a second elastic member 127 driving the first unlocking member 125 to be reset.

First elastic members 126 may be respectively mounted in a direction in which the two first snap-in connectors 124 are away from each other, and may drive the two first snap-in connectors 124 to approach each other. That is, the two first snap-in connectors 124 may move toward each other by the driving of the two first elastic members 126. The first unlocking member 125 may have a wide portion 1251 and a narrow portion 1252. The two first snap-in connectors 124 may abut against the wide portion 1251 from both sides under the action of the first elastic member 126 to keep a steady distance therebetween without an external force.

The second elastic member 127 may be connected to the first unlocking member 125 for keeping the wide portion 1251 of the first unlocking member 125 between the two first snap-in connectors 124. That is, the wide portion 1251 of the first unlocking member 125 may be impelled to move to the region between the two first snap-in connectors 124 by the elastic force of the second elastic member 127.

The first unlocking member 125 may be exposed from the housing 120, so that the position of the first unlocking member 125 can be changed by a user to enable the two first snap-in connectors 124 to abut on the narrow portion 1252 to change the distance between the two first snap-in connectors 124. The first unlocking member 125 may move inward or out of the housing 120 according to the arrangement of the second elastic member 127, so that the wide portion 1251 of the first unlocking member 125 may be away from the middle of the region between the two first snap-in connectors 124 to move the narrow portion 1252 of the first unlocking member 125 to the middle of the region between the two first snap-in connectors 124. The first elastic member 126 may drive the two first snap-in connectors 124 to move relative to each other so as to abut against the narrow portion 1252, thereby reducing the distance between the two first snap-in connectors 124. Since the hook portions 1241 of the two first snap-in connectors 124 are arranged in a direction away from each other, when the distance between the two first snap-in connectors 124 becomes shorter, the two hook portions 1241 can be disengaged from their corresponding mounting parts on the portable ultrasonic apparatus 2000 (for example the bayonets of the portable ultrasonic apparatus 2000), thereby unlocking.

When the portable ultrasonic apparatus 2000 is detachably fixed to the shareable battery pack 100, referring to FIGS. 5, 6 and 8, the first unlocking member 125 is moved by the user (for example, the first unlocking member 125 is pressed and moved toward the housing 120, or the first unlocking member 125 may be pulled outward in other embodiments), the first unlocking member 125 may compress the second elastic member 127 to make the wide portion 1251 on the inner side to move inward to separate from the two first snap-in connectors 124 and the narrow portion 1252 on the outer side to move inwardly to the region between the two first snap-in connectors 124, thereby pressing against the narrow portion 1252 by the two first snap-in connectors 124 with the action of the first elastic member 126. In this respect, the distance between the two first snap-in connectors 124 may become shorter to be inserted into the corresponding installation part of the portable ultrasonic apparatus 2000, such as the bayonet.

When the first unlocking member 125 is released by the user, the first unlocking member 125 may be reset under the action of the second elastic member 127, thereby moving the wide portion 1251 of the first unlocking member 125 to the region between the two first snap-in connectors 124 again to stretch the two first snap-in connectors 124 outwards to fasten to their corresponding mounting parts of the portable ultrasonic apparatus 2000 (for example, the opening wall of the bayonet of the portable ultrasonic apparatus 2000). In this way, clamping and fixing therebetween may be realized. The first unlocking member 125 may be pressed again to unlock.

Of course, the corresponding mounting parts of the portable ultrasonic apparatus 2000 may directly be abutted against the two first snap-in connectors 124 to force the first snap-in connector 124 to exert pressure on the first unlocking member 125 to overcome stress of the second elastic member 127 on the first unlocking member 125. In this way, the first unlocking member 125 is moved to drive the narrow portion 1252 to be located between the two first snap-in connectors 124, changing the distance between the two first snap-in connectors 124. When the first snap-in connectors 124 are buckled into the corresponding installation parts (such as the bayonets) of the portable ultrasonic apparatus 2000, the first snap-in connectors 124 may be released, and the second elastic member 127 may cause the first unlocking member 125 to reset, thereby releasing the two first snap-in connectors again to fasten the portable ultrasonic apparatus 2000.

An inclined guide surface may be provided between the wide portion 1251 and the narrow portion 1252 of the first unlocking member 125, so that the wide portion 1251 and the narrow portion 1252 can smoothly move between the two first snap-in connectors 124. The first elastic element 126 and the second elastic element 127 may be but are not limited to springs (so do other elastic elements mentioned below). The first snap-in connectors 124 may also be controlled in other forms. For example, the first snap-in connectors 124 and the first unlocking member 125 may be an integral structure or the two may be in transmission connection.

Referring to FIG. 8, in some embodiments, an auxiliary locking member 1281 arranged on the first unlocking member 125 and an auxiliary locking elastic member 1282 arranged vertically may also be provided. The auxiliary locking member 1281 may be configured to fixed at the locked position. In an embodiment, the first unlocking member 125 may have a matching portion, such as a limit opening. The auxiliary locking member 1281 can be assembled to the mating portion, for example, it may be inserted into the limit opening to lock the first unlocking member 125 and stop the movement of the first unlocking member 125 from the locked position to the unlocked position, thereby preventing the portable ultrasonic apparatus 2000 and the shareable battery pack 100 from being damaged due to being unintentionally unlocked each other during being carried (such as they are carried on the hand). The auxiliary locking elastic member 1282 may be mounted on the auxiliary locking member 1281 to give the auxiliary locking member 1281 an elastic pre-tightening force, so that the auxiliary locking member 1281 may keep the first unlocking member 125 locked. The auxiliary locking member 1281 may be movably mounted on the housing 120, so that the pre-tightening force generated by the auxiliary locking elastic member 1282 can be overcome via an external force, thereby moving the position of the auxiliary locking member 1281. In this way, the first unlocking member 125 may be unlocked and further be used to unlock the first snap-in connector 124.

Referring to FIGS. 5 and 6, in an embodiment, the first snap-in connector 124 may be protruded from the top wall of the housing 120 and the first unlocking member 125 may be protruded from the side wall of the housing 120, so that the portable ultrasonic apparatus 2000 and the shareable battery pack 100 may be locked and unlocked easily. The shareable battery pack 100 may be provided an unlocking opening 129 on the side wall thereof, and the first unlocking member 125 may be arranged in the unlocking opening 129. The unlocking port 129 may also be used as the second mounting part of the shareable battery pack to be locked by the trolley 200 when needed, for example, it may cooperate with the second snap-in connector mentioned later to fix the shareable battery pack 100 on the trolley 200. The portable ultrasonic apparatus 2000 may be conveniently mounted on the top of the shareable battery pack 100. The first unlocking member 125 may be unlocked from the side wall of the shareable battery pack 100 to remove the portable ultrasonic apparatus 2000 when unlocking.

Further, the charging connector 131 and the discharging connector 132 may be coupled to the portable ultrasonic apparatus 2000 and/or the trolley 200 in a wired or wireless manner. Please refer to FIGS. 5 and 6, in an embodiment, at least one first magnetic socket 133 having a first magnetic member that is convenient to attract the portable ultrasonic apparatus 2000 and/or the trolley 200 may further be included. The charging connector 131 and the discharging connector 132 may be arranged in the same or different first magnetic sockets 133 to supply power to the portable ultrasonic apparatus 2000 and charge to the battery 110.

The first magnetic member can attract the portable ultrasonic apparatus 2000 and/or the trolley 200 within a certain range. As long as the portable ultrasonic apparatus 2000 and/or the trolley 200 is within this range, it may be automatically attracted by the first magnetic socket 133 to corresponding docking position. Of course, the portable ultrasonic apparatus 2000 and/or the trolley 200 may be provided with a unit that is magnetically matched with the first magnetic member. The first magnetic socket 133 may have a rigid wire which may be upright and can slightly swing. When the portable ultrasonic apparatus 2000 and/or the trolley 200 are assembled in place, the wire may be automatically attracted into the connector of the portable ultrasonic apparatus 2000 and/or the trolley 200 with magnetic force to realize automatic mating.

The shareable battery pack 100 provided above may be used alone, or combined with the trolley 200 to form a power supply system 1000, or combined with the trolley 200 and the portable ultrasonic apparatus 2000 to form a portable ultrasonic system for use.

Further, referring to FIGS. 3 and 9 to 12, a trolley 200 for a portable ultrasonic apparatus 2000 may be provided in an embodiment. The trolley 200 may include a base 210, a support table 220 for supporting the shareable battery pack 100, a power supply 230, and a control circuit 240.

The base 210 may serve as a mounting seat for the trolley 200. The support table 220 may be mounted on the base 210 and may provide with an installation part for bearing the shareable battery pack 100 and a third mounting part detachably connected with the shareable battery pack 100 and/or the portable ultrasonic apparatus 2000.

The shareable battery pack 100 and the portable ultrasonic apparatus 2000 may be detachably mounted on the installation part. If necessary, the portable ultrasonic apparatus 2000 may be removed, or the portable ultrasonic apparatus 2000 and the shareable battery pack 100 may, as a whole, be removed together for use.

Figure 12:
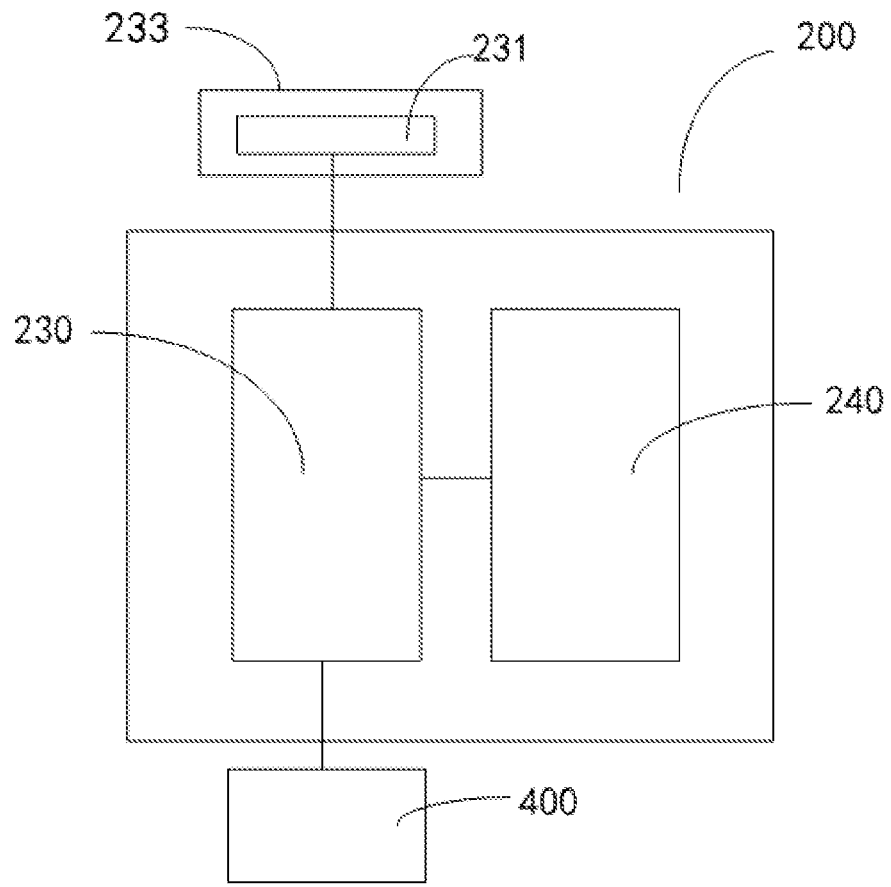
FIG. 12 is a block diagram that schematically illustrates the circuit structure of a trolley in an embodiment according to the present disclosure.

Please refer to FIG. 12, the power supply 230 itself may store electric energy and be externally coupled to the power supply 400 for charging. The power supply 230 may have an output connector 231 for docking with the shareable battery pack 100 or the portable ultrasonic apparatus 2000 to supply power to the shareable battery pack 100 or the portable ultrasonic apparatus 2000. The control circuit 240 may be connected to the power supply 230 to control the power supply 230 to power the shareable battery pack 100 or the portable ultrasonic apparatus 2000.

In another embodiment, the power supply 230 may not be provided. The trolley 200 may include a charging lead wire having an electric input terminal and an electric output terminal. The electrical output terminal may be configured to be electrically connected with an external charging device, and the electrical input terminal may be configured to dock with the shareable battery pack 100 or the portable ultrasonic apparatus 2000 to conduct the current of the external charging device to the shareable battery pack 100 or the portable ultrasonic apparatus 2000. In this embodiment, the charging lead wire may only be a conductive tool for conducting current, and the external charging device may be a charging device such as a power adapter.

Of course, in other embodiments, the power supply 230 and the charging lead may not be provided, that is, the trolley 200 may only be used to support the shareable battery pack 100 and the portable ultrasonic apparatus 2000, and the shareable battery pack 100 and the portable ultrasonic apparatus 2000 may directly couple to an external charging device for charging.

In addition, in an embodiment, the trolley 200 may also include a power supply circuit for coupling the shareable battery pack 100 or the portable ultrasonic apparatus 2000 to an external charging device to conduct current to the shareable battery pack 100 or a portable ultrasonic apparatus 2000 for power supply.

In some embodiments, the shareable battery pack 100 may also include some other conventional units, such as a reel, a filter, a fuse and AC indicator board, etc., and may even have a wireless charging receiving unit, etc., which will not be described in detail here.

Further, the output connector 231 may be connected to the portable ultrasonic apparatus 2000 and/or the shareable battery pack 100 in a wired or wireless manner. Please refer to FIGS. 9 and 12, in an embodiment, at least one second magnetic socket 233 having a second magnetic member that is convenient to attract the portable ultrasonic apparatus 2000 and/or the shareable battery pack 100 may further be included. The output connector 231 may be arranged in the second magnetic socket 233 to charge the portable ultrasonic apparatus 2000 and/or the shareable battery pack 100.

The second magnetic member may attract the portable ultrasonic apparatus 2000 and/or the shareable battery pack 100 within a certain range. As long as the portable ultrasonic apparatus 2000 and/or the shareable battery pack 100 is within this range, it may be automatically attracted by the second magnetic socket 233 into a corresponding docking position. Of course, the portable ultrasonic apparatus 2000 and/or the shareable battery pack 100 may be provided with a unit that may magnetically cooperate with the second magnetic member (for example, the shareable battery pack 100 may have a first magnetic socket 133). The second magnetic socket 233 may have a rigid wire, which may be upright and can slightly swing. After the portable ultrasonic apparatus 2000 and/or the shareable battery pack 100 are assembled in place, the wire may be automatically attracted into the connector of the portable ultrasonic apparatus 2000 and/or the shareable battery pack 100 with magnetic force to realize automatic mating.

Further, in an embodiment, the installation part may be on the top wall of the support table 220 so as to enable the shareable battery pack 100 to be detachably installed on the top wall of the support table 220. Such design can facilitate the shareable battery pack 100 to be detached and attach to the trolley 200, so that the shareable battery pack 100 and the portable ultrasonic apparatus 2000 fixed therewith may be removed and replaced quickly by the user.

The installation part may be of various types of mounting structures, such as a supporting surface, a supporting bracket, a clamping structure and the like. Please refer to FIGS. 9 and 11, in an embodiment, the installation part may be provided with a recessed installation cavity 221 having an open at least at the top to accommodate the shareable battery pack 100. The user can insert the shareable battery pack 100 from the top of the installation cavity 221.

In some embodiments, at least one side of the installation cavity 221 may be opened, so that the shareable battery pack 100 may be put in from the side.

Figure 9:
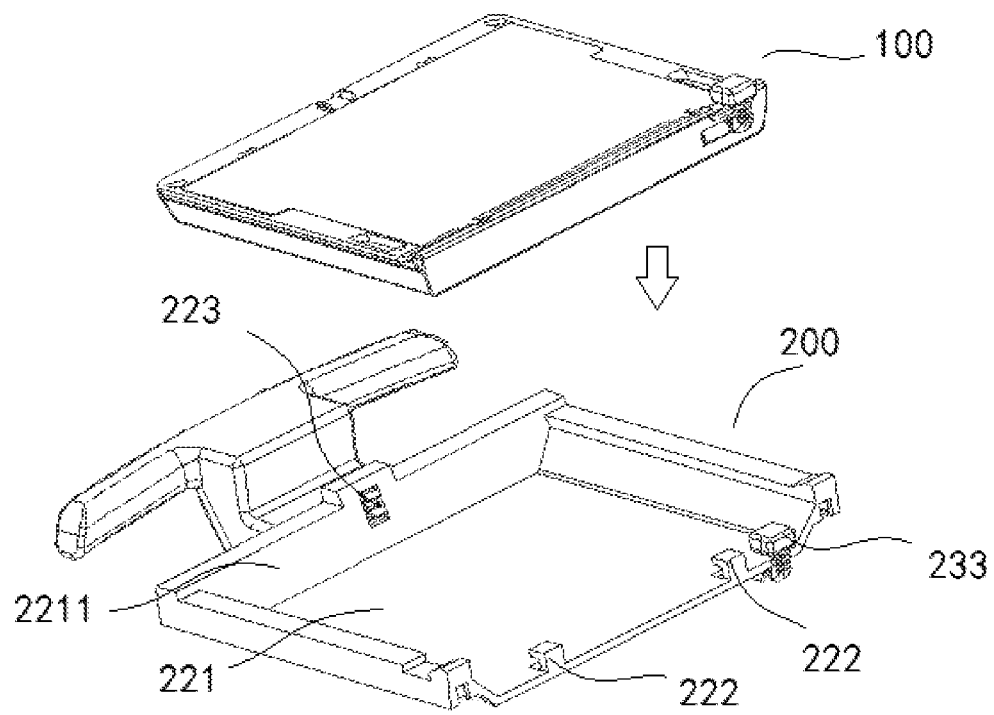
FIG. 9 schematically illustrates assembling a trolley and a shareable battery pack in an embodiment according to the present disclosure.
Figure 11:
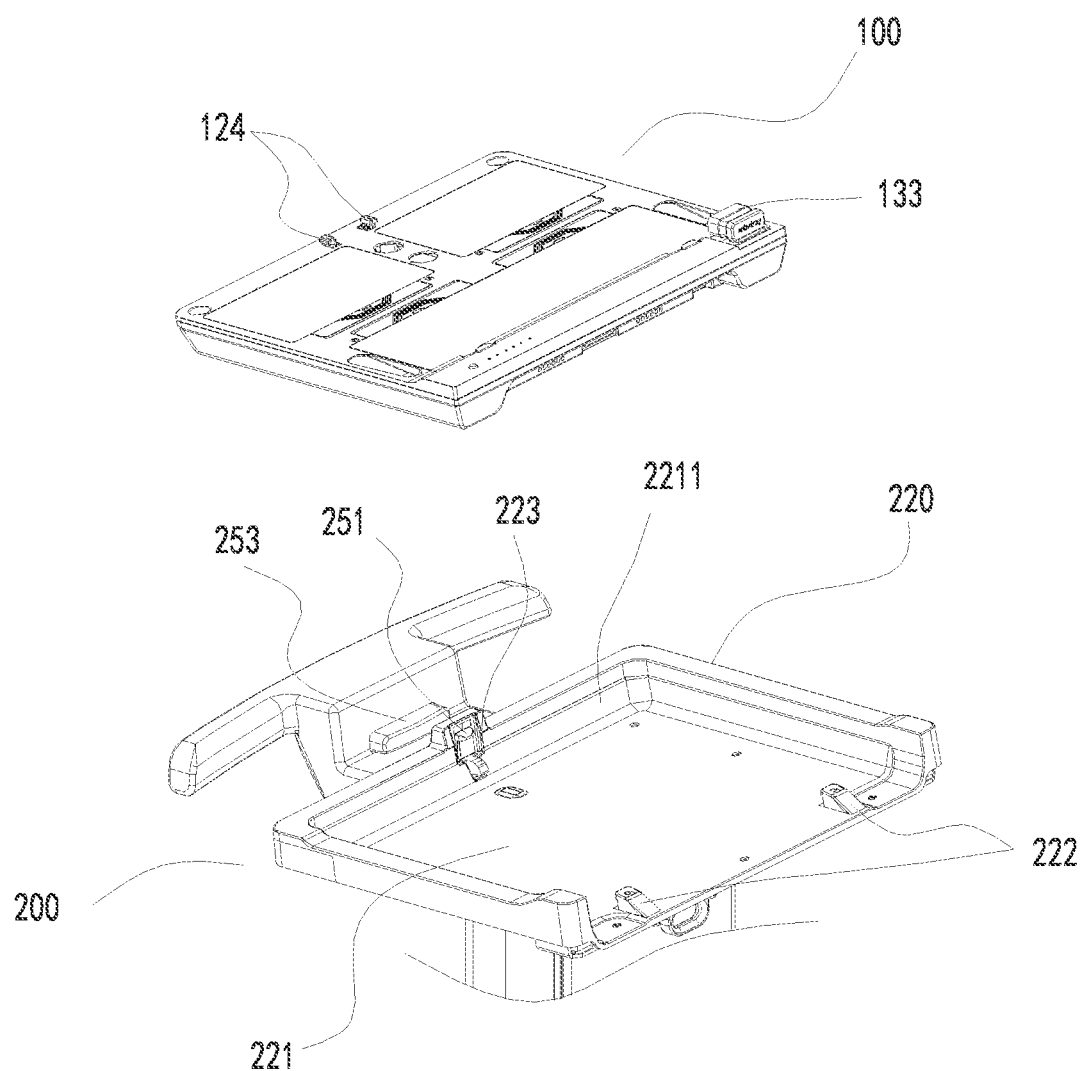
FIG. 11 schematically illustrates the assembly of the shareable battery pack with the trolley in another embodiment according to the present disclosure.

Further, referring to FIGS. 9 and 11, in an embodiment, at least one side wall 2211 of the installation cavity 221 may be inclined in an outside-in manner to enable the shareable battery pack 100 to be slid into the installation cavity 221 along the side wall 2211. The inclined side wall 2211 may guide the shareable battery pack 100 to move into the installation cavity 221. In this respect, the shareable battery pack 100 can be smoothly replaced without aligning the shareable battery pack 100 completely with the installation cavity 221, improving the convenience of installation of the shareable battery pack 100.

Figure 10:
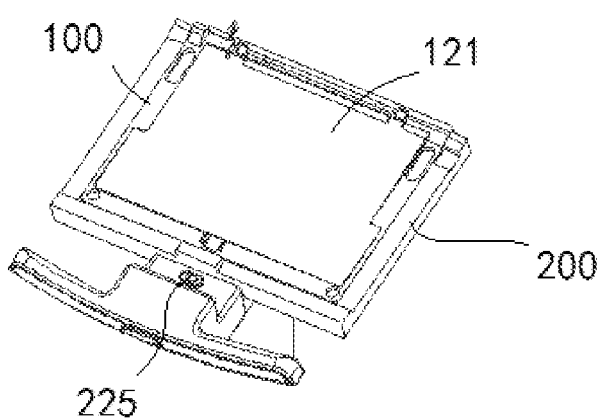
FIG. 10 schematically illustrates the assembly, as shown in FIG. 9, of the shareable battery pack with the trolley.

In order to limit the position of the shareable battery pack 100, please refer to FIGS. 9 to 11, in an embodiment, the installation cavity 221 may be provided with a raised second limiting portion 222 that is arranged in a direction in which the shareable battery pack is inserted. The second limiting portion 222 may be a structure such as a bump, a barb, or a rib. The limit may be formed by the second limiting portion 222 which may be more than one surrounding the shareable battery pack 100 from one or more positions.

The second limiting portion 222 may be arranged on the opposite side of the inclined side wall 2211 to limit the installation part of the shareable battery pack 100. When one side of the installation cavity 221 is open, as shown in FIGS. 9 and 11, the second limiting portion 222 may be arranged on this side to prevent the shareable battery pack 100 from slipping off this side.

Further, the third mounting part may be primarily used to detachably fix the shareable battery pack 100 to the trolley 200. Please refer to FIGS. 9 to 11, in an embodiment, the third mounting part may have a second snap-in connector 223 used to buckle the shareable battery pack 100. The second snap-in connector may have a first hook portion 2231 (shown in FIGS. 13 and 14) for buckling the second mounting part on the shareable battery pack 100. The second mounting part may also be a buckle structure, or may also be a buckling seat, bayonet or other structure that can be buckled by the second snap-in connector 223.

Of course, inversely, the second mounting part may also be provided with a unit similar to the snap-in structure of the second snap-in connector 223 to fasten the third mounting part of the trolley 200. The third mounting part may be a buckling seat, a bayonet or other structures.

Figure 13:
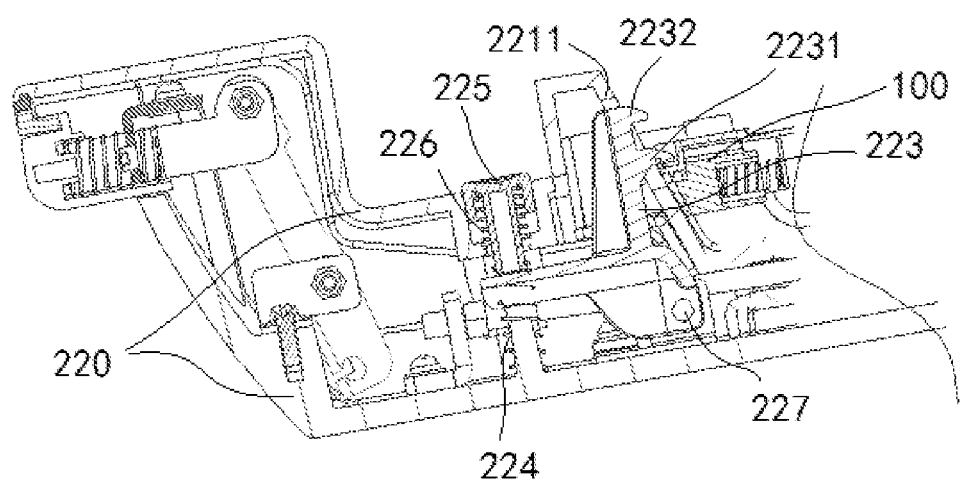
FIG. 13 is a partial cross-sectional view (illustrating the connection between a second snap-in connector and a shareable battery pack) of a trolley in an embodiment according to the present disclosure.
Figure 14:
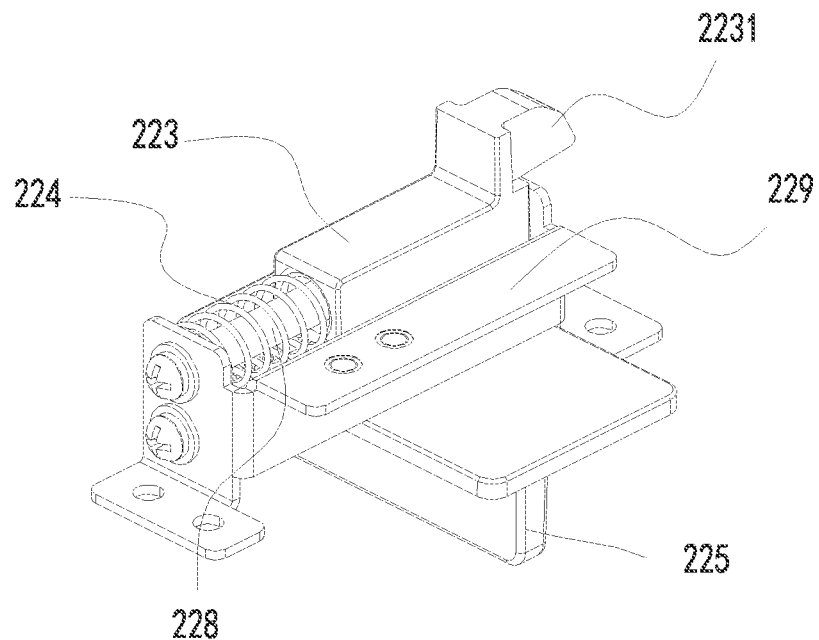
FIG. 14 schematically illustrates the structure of a second snap-in connector of a trolley in another embodiment according to the present disclosure.
Figure 15:
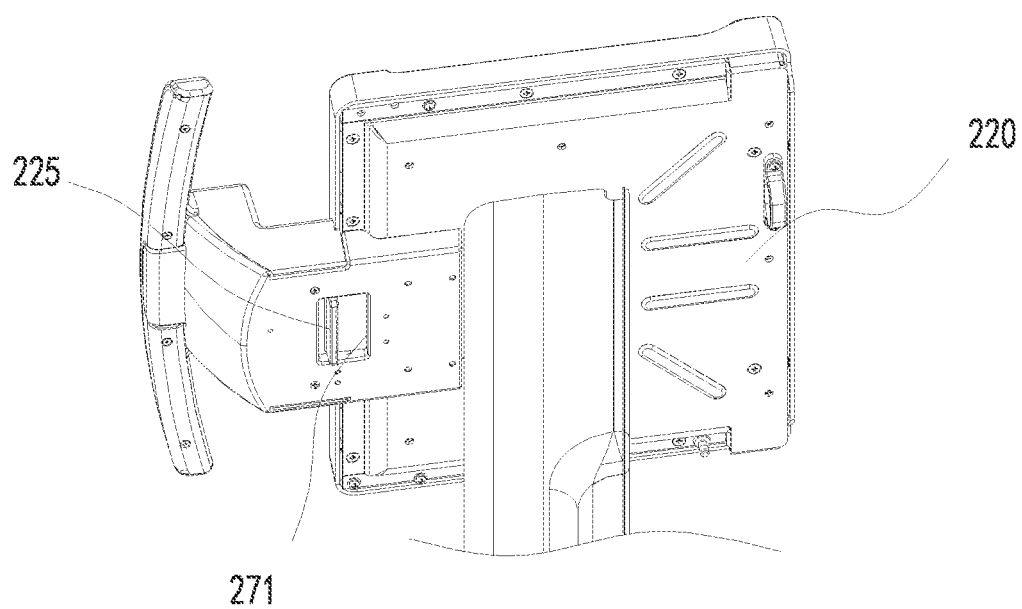
FIG. 15 schematically illustrates the position of a second unlocking member on a support table in another embodiment according to the present disclosure.

Further, please refer to FIGS. 13 and 14, in an embodiment, the third mounting part may further have a third elastic member 224 and a second unlocking member 225 for resetting the second snap-in connector 223. The third elastic member 224 may drive the second snap-in connector 223 to extend from the outer wall of the support table 220 (for example, the side wall 2211 of the installation cavity 221), and the second unlocking member 225 may be in transmission connection with the second snap-in connector 223 to enable the second snap-in connector 223 to move into the support table 220 by means of the second unlocking member 225.

The second unlocking member 225 and the second snap-in connector 223 may be integrally connected, or it may be designed as a separate body and the two may be connected by transmission, that is, the second unlocking member 225 may drive the second snap-in connector 223 to move into the support table 220, which can be realized by various transmission structures.

In an embodiment, referring to FIGS. 9, 11, 13 and 17, the installation part may be the installation cavity 221 having at least one side wall 2211 inclined in an outside-in manner. The second snap-in connector 223 may be arranged on the inclined side wall 2211 and may have a first hook portion 2231 for buckling the shareable battery pack 100. The top wall of the first hook portion 2231 may be inclined downwardly to form the first guide surface, which is convenient for guiding the shareable battery pack 100 downwardly into the installation cavity 221. The shareable battery pack 100 may be inserted directly into the installation cavity 221 along the oblique side wall 2211, pressing the first hook portion 2231 downward to a certain extent. In this respect, the first hook portion 2231 and/or the second mounting part of the shareable battery pack 100 may be deformed to buckle the first hook portion 2231 to the second mounting part of the shareable battery pack 100 (such as the unlock port 129).

Alternatively, the second unlocking member 225 may be driven to the unlock position by the user, the shareable battery pack 100 may then be put into the shareable battery pack 223, and the second snap-in connector 223 may be released to buckle the second mounting part of the shareable battery pack 100 under the action of the third elastic member 224.

When unlocking, the second snap-in connector 223 may be moved to the unlocked position, and the shareable battery pack 100 may then be detached.

Please refer to FIG. 13, in an embodiment, the second snap-in connector 223 may be rotatably mounted in the support table 220, and the second unlocking member 225 may vertically abut one end of the second snap-in connector 223. The second unlocking member 225 may be provided with a fourth elastic member 226 for resetting the second unlocking member 225 upward. When the second unlocking member 225 is pressed down, the second snap-in connector 223 may be driven to rotate around the rotating shaft 227 to retract the second snap-in connector 223 into the support table 220. When the second unlocking member 225 is released, the fourth elastic member 226 may drive the second unlocking member 225 to reset, and the third elastic member 224 may drive the second snap-in connector 223 to reset.

The second snap-in connector 223 may be mounted on the support table 220 in sliding manner or in other ways instead of the rotation connection.

In one embodiment, the second snap-in connector 223 may be slidably mounted in the support table 220 and connected to the second unlocking member 225 by a connecting member having a wide portion and a narrow portion. The second unlocking member 225 may substantially vertically abut on the connecting member 225, and one end of the second snap-in connector may substantially horizontally abut on the connecting member. The third elastic member 224 using for resetting the second snap-in connector may be arranged on the same horizontal line as the second snap-in connector and the connecting member. The second unlocking member 225 may be provided with a fourth elastic member 226 used for resetting the second unlocking member 225 upward. When the second unlocking member 225 is pressed, the connecting member may move downward to enable the second snap-in connector 223 to abut against the narrow portion of the connecting member to drive the second snap-in connector to be withdraw into the support table 220. When the second unlocking member 225 is released, the fourth elastic member 226 may drive the second unlocking member 225 to reset and the third elastic member 224 may drive the second snap-in connector 223 to reset. In this respect, the second snap-in connector 223 may abut against the wide portion of the connecting member, and the second snap-in connector 223 can buckle the shareable battery pack.

Referring to FIGS. 11 and 14, in an embodiment, the second snap-in connector 223 may be slidably mounted on a corresponding sliding shaft 228 which is mounted on a supporting seat 229. The sliding shaft 228 and the supporting seat 229 may be mounted in the support table 220, and the supporting seat 229 may be fixedly mounted on the support table 220. The third elastic member 224 may be arranged on the sliding shaft 228 in a nested manner and abut against one end of the second snap-in connector 223. The second unlocking member 225 and the second snap-in connector 223 may be fixedly connected as a whole without needing the fourth elastic member 226, and the second snap-in connector 223 and the second unlocking member 225 may be reset by the third elastic member 224. In this embodiment, the second snap-in connector 223 and the second unlocking member 225 may be moved in the same direction. Referring to FIG. 5, the second unlocking member 225 may be arranged in an opening 271 of the bottom shell of the support table 200 and protruded downward, and it may also certainly be arranged at other positions of the support table 200 for the user to manipulate.

Figure 17:
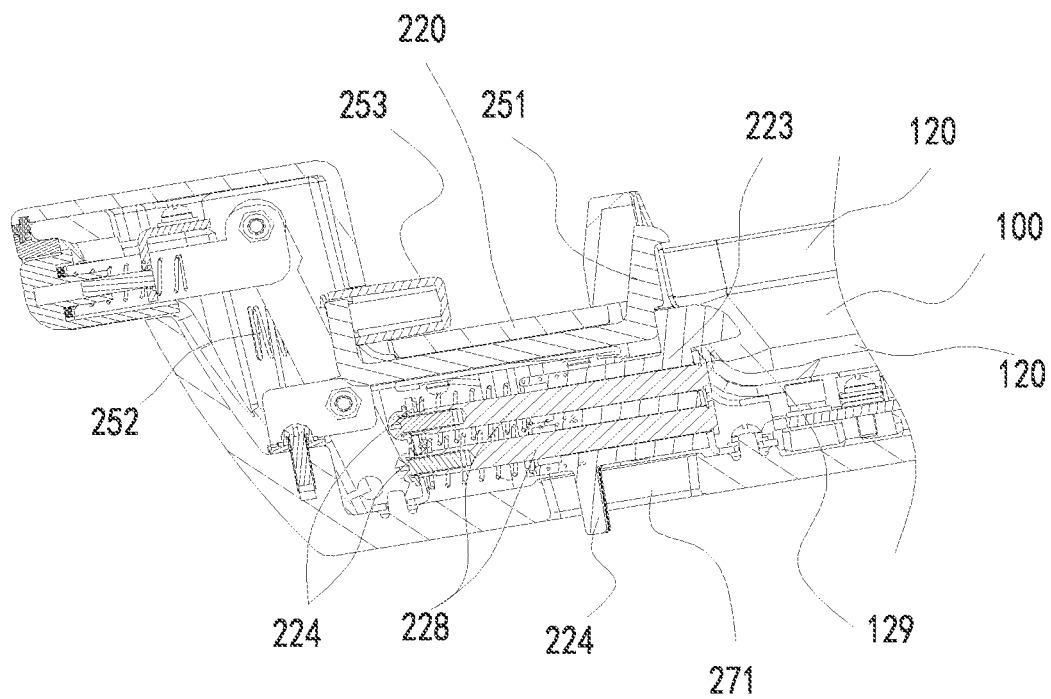
FIG. 17 is a cross-sectional view that illustrates the matching among the second and third snap-in connectors of a trolley and a shareable battery pack in an embodiment according to the present disclosure.

The second snap-in connector 223 may only be used to fix the portable ultrasonic apparatus 2000 (as shown in FIG. 17) or to fix both the portable ultrasonic apparatus 2000 and the shareable battery pack 100 at the same time (as shown in FIG. 13).

Referring to FIGS. 9 and 13, in an embodiment, the second snap-in connector may be provided with a first hook portion 2231 for buckling the shareable battery pack 100 and a second hook portion 2232 arranged above the first hook portion for buckling the portable ultrasonic apparatus 2000. That is, the second snap-in connector 223 can fasten the portable ultrasonic apparatus 2000 and the shareable battery pack 100 at the same time. When unlocking, both the portable ultrasonic apparatus 2000 and the shareable battery pack 100 can be unlocked simultaneously by means of the second unlocking member 225.

After the portable ultrasonic apparatus 2000 and the shareable battery pack 100 are installed on the trolley 200, the portable ultrasonic apparatus 2000 and the shareable battery pack 100 may still remain in a fixed state, or they may be in an unlocked state.

In an embodiment, when the first hook portion cooperates with the shareable battery pack 100, the first hook portion 2231 may also trigger the first unlocking member 125 to move to the unlocking position to unlock the shareable battery pack 100 and the portable ultrasonic apparatus 2000 after the shareable battery pack 100 is mounted on the trolley 200.

Please refer to FIGS. 11 and 14 to 18, in one embodiment, the second snap-in connector 223 may only be used to fix the portable ultrasonic apparatus 2000. In this respect, in order to lock the portable ultrasonic apparatus 2000, the third mounting part of the trolley 200 may further have a third snap-in connector 251 for buckling the portable ultrasonic apparatus 2000. That is, the trolley 200 may fix the shareable battery pack 100 by the second snap-in connector 223 and buckle the portable ultrasonic apparatus 2000 by the third snap-in connector 251.

Please referring to FIGS. 14 to 18, in an embodiment, the third mounting part may further have a fifth elastic member 252 and a third unlocking member 253 for resetting the third snap-in connector 251. The fifth elastic member 252 may drive the third snap-in connector 251 to protrude from the outer wall (such as the side wall 2211) of the support table 220 to buckle the portable ultrasonic apparatus 2000.

Figure 16:
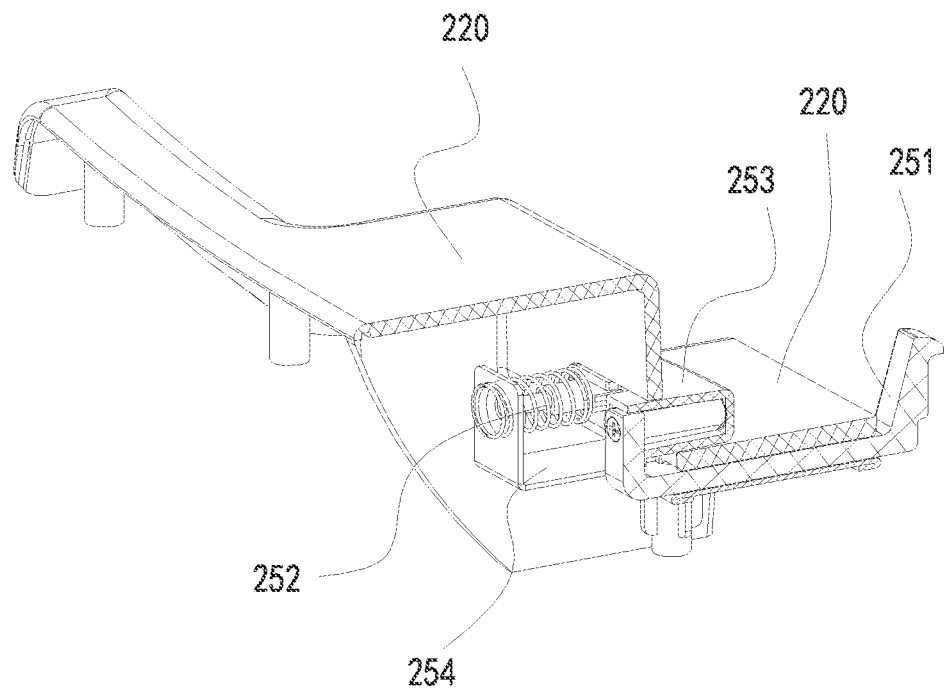
FIG. 16 schematically illustrates the structure of a third snap-in connector in an embodiment according to the present disclosure.

The third unlocking member 253 and the third snap-in connector 251 may be such as integrally formed as an integral structure. The third unlocking member 253 and the third buckle 251 may certainly also be separately and connected in transmission, that is, the third unlocking member 253 may drive the third snap-in connector 251 to move into the support table 220, which can be realized by various transmission structure. As shown in FIG. 16, the third unlocking member 253 and the third snap-in connector 251 are fixedly connected as one body, installed on a sliding support 254 and are driven and reset by the fifth elastic member 252. The sliding support 254 may be fixedly installed in the support table 220. In some embodiments, the third snap-in connector 251 may also be provided with a pressure adjusting holder to adjust the pre-tightening force.

Figure 18:
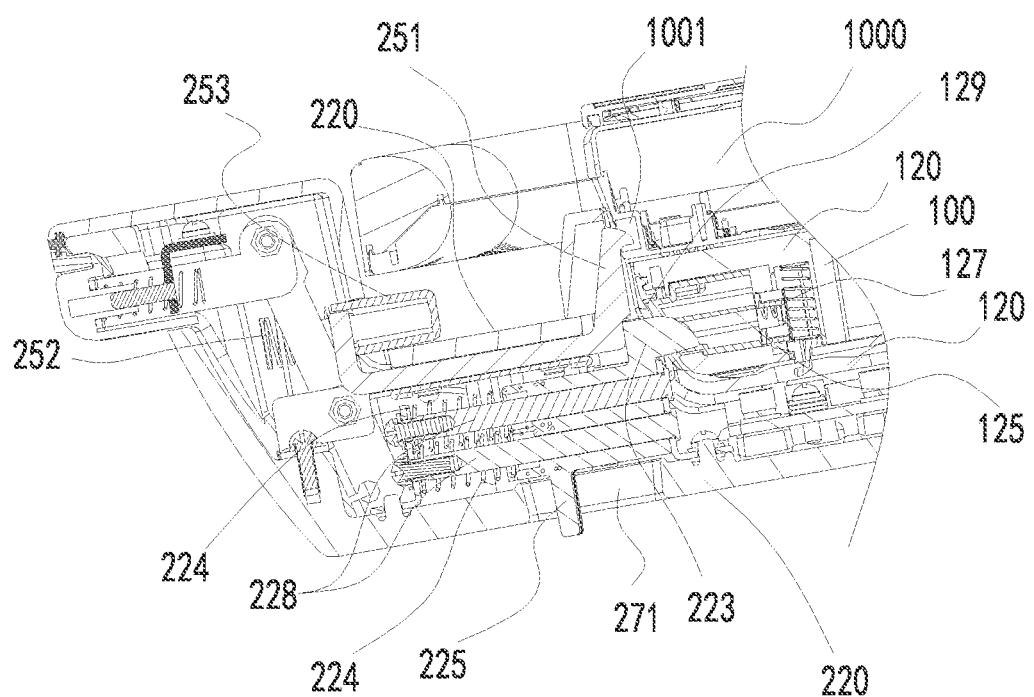
FIG. 18 is a cross-sectional view that illustrates the matching among the second and third snap-in connectors of the trolley, a shareable battery pack and a portable ultrasonic apparatus in an embodiment according to the present disclosure.

Referring to FIGS. 17 and 18, in a better embodiment, when the shareable battery pack 100 and the portable ultrasonic apparatus 2000 are installed on the trolley 200, the second snap-in connector 223 in the locked position can drive the first mounting part of the shareable battery pack 100 to turn to the unlocked position, so that the shareable battery pack 100 and the portable ultrasonic apparatus 2000 are in the unlocked state.

For example, as shown in FIGS. 17 and 18, when the shareable battery pack 100 and the portable ultrasonic apparatus 2000 are installed on the trolley 200, in the case of the first mounting part of the shareable battery pack 100 adopting the structure shown in FIG. 8, the second snap-in connector 223 may abut against the first unlocking member 125 of the first mounting part and the first snap-in connector 124 may be moved to the unlocked position by the first unlocking member 125, unlocking the shareable battery pack 100 and the portable ultrasonic apparatus 2000.

Such structure can bring advantages that it can be chosen according to needs whether to take out the portable ultrasonic apparatus 2000 separately or to take out the shareable battery pack 100 and the portable ultrasonic apparatus 2000 together as a whole. For example, in this case, the portable ultrasonic apparatus 2000 may be separately unlocked by controlling the third unlocking member 253 to take out the portable ultrasonic apparatus 2000 alone, or the second unlocking member 225 may be unlocked first to unlock the shareable battery pack 100 and turn the shareable battery pack 100 and the portable ultrasonic apparatus 200 to be in the locked state, thereby unlocking the third unlocking member 253 and taking out the shareable battery pack 100 and the portable ultrasonic apparatus 2000 together as a whole.

Further, in order to detach conveniently the shareable battery pack 100 and the portable ultrasonic apparatus 2000 together as a whole, please refer to FIGS. 17 and 18, in an embodiment, the third snap-in connector 251 may be located at the path where the second snap-in connector 223 are retracted, so that the second snap-in connector 223 can drive the third snap-in connector 251 to move in the unlocking direction together when the second snap-in connector 223 is unlocked. Therefore, when the shareable battery pack 100 and the portable ultrasonic apparatus 2000 need to be detached as a whole, only the second unlocking member 225 needs to be driven to simultaneously unlock the second snap-in connector 223 and the third snap-in connector 251 together.

As shown in FIGS. 17 and 18, the second snap-in connector 223 may be located below the third snap-in connector 251, and the third snap-in connector 251 is at least partially on the movement path of the second snap-in connector 223. Therefore, when the second snap-in connector 223 is moved in the unlocking direction, it may inevitably impact on the third snap-in connector 251 and drive the third snap-in connector 251 to move in the unlocking direction together.

The unlocking movement directions of the second snap-in connector 223 and the third snap-in connector 251 may be the same. Certainly, they may also be different, and in the latter case they may be interlinked via structural design to enable the second snap-in connector 223 to drive the third snap-in connector 251 to move in the unlocking direction together.

Further, referring to FIGS. 17 and 18, in an embodiment, the installation part may have a recessed installation cavity 221, and the third snap-in connector 251 may be slidably arranged in the support table 220. The third unlocking member 253 may be exposed outside the support table 220 and be in transmission connection with the third snap-in connector 251. The fifth elastic member 252 may act on the third snap-in connector 251 to drive the third snap-in connector 251 to reset from the installation cavity 221 to the position where it protrudes from the side wall 2211.

A trolley provided in one embodiment may include a base, a support table mounted on the base and a locking arrangement mounted on the support table. As shown in FIG. 13, the locking arrangement may include a second snap-in connector 223, a third elastic member 224, and a second unlocking member 225. The second snap-in connector may have at least a first hook portion 2231 for buckling the first member and a second hook portion 2232 arranged above the first hook portion for buckling a second member. A first end of the third elastic member 224 may abut on the support table, and a second end of the third elastic member 224 may abut on an end of the second snap-in connector 223 away from the first and second hook portions. The third elastic member 224 may drive the second snap-in connector 223 to be in the locked state, and the second unlocking member 225 may be in transmission connection with the second snap-in connector 223 which may drive the second snap-in connector 223 to be in the unlocked state via the second unlocking member 225.

In an embodiment, besides the components mentioned in the aforesaid embodiments, it may further include a rotating shaft 227, and the second snap-in connector 223 may be rotatably connected to the support table with the rotating shaft as the axle center.

In an embodiment, the second unlocking member 225 may vertically abut one end of the second snap-in connector 223 away from the first and second hook portions, and the second unlocking member 225 may be provided with a fourth elastic member 226 for resetting the second unlocking member 225 upward.

A trolley provided in one embodiment may include a base, a support table arranged on the base and a locking arrangement arrange on the support table. As shown in FIG. 18, the locking arrangement may include at least a second snap-in connector 223, a third snap-in connector 251, a third elastic member 224, and a second unlocking member 225. The second snap-in connector 223 may have a first hook portion 2231 for fastening to a first member, and the third snap-in connector 251 may have a second hook portion 2232 for fastening to a second member. One end of the third elastic member 224 may abut against the side wall of the support table, and the other end of the third elastic member 224 may abut against an end of the third elastic member 224 away from the second snap-in connector 223. The third elastic member 22 may drive the snap-in connector 223 to be in the locked state, the second unlocking member 225 may be in transmission connection with the second snap-in connector 223 and turn the second snap-in connector to be in the unlocked state. The third snap-in connector 251 may be on a path in which the second snap-in connector 223 is withdrawn, so that when the second snap-in connector 223 is unlocked, it can drive the third snap-in connector 251 to move in the unlocking direction together.

In an embodiment, the locking arrangement may further have a fifth elastic member 252 and a third unlocking member 253 for resetting the third snap-in connector. One end of the fifth elastic member 252 may abut against the side wall of the support table, and the other end of the fifth elastic member may abut against the third unlocking member 253. The fifth elastic member 252 may drive the third snap-in connector 251 to be in the locked state, and the third unlocking member 253 and the third snap-in connector 251 may be connected as a whole or in a transmission connection to enable the third snap-in connector 251 to be in the unlocked state by means of the third unlocking member 253.

The principle and implementation of the present disclosure have been described above with reference to specific embodiments, which are merely provided for the purpose of understanding the present disclosure and are not intended to limit the present disclosure. It will be possible for those skilled in the art to make variations based on the principle of the present disclosure.

What is claimed is:

1. A shareable battery pack for a portable ultrasonic apparatus, comprising:
   at least one battery for storing electrical energy;
   a housing having a holding cavity in which the at least one battery is accommodated, the housing comprising a first mounting part detachably coupled to the portable ultrasonic apparatus and a second mounting part detachably coupled to a trolley, wherein the shareable battery pack is capable of being installed on an installation part of the trolley, and when the shareable battery pack is detachably connected to the portable ultrasonic apparatus to form an integral unit, the integral unit is capable of being detachably mounted on the trolley through installation of the shareable battery pack on the installation part, with the shareable battery pack being on top of the trolley and the portable ultrasonic apparatus being on top of the shareable battery pack;

a charging and discharging circuit electrically connected to the at least one battery and comprising a charging connector for charging the at least one battery and a discharging connector for discharging the at least one battery to charge the portable ultrasonic apparatus; and a control circuit for controlling the charging and discharging circuit to charge and discharge.

2. The shareable battery pack according to claim 1, wherein the charging and discharging circuit comprises a discharge equalization circuit and a charge equalization circuit to control discharging and charging the at least one battery.

3. The shareable battery pack according to claim 1, wherein the housing comprises a supporting member on which the portable ultrasonic apparatus is placed.

4. The shareable battery pack according to claim 3, wherein the supporting member comprises a supporting surface that matches a bottom of the portable ultrasonic apparatus.

5. The shareable battery pack according to claim 4, wherein the supporting surface comprises a convex guiding portion or a concave guiding portion for enabling the portable ultrasonic apparatus to move on the supporting surface along the convex guiding portion or the concave guiding portion.

6. The shareable battery pack according to claim 4, further comprising a raised first limiting portion arranged in a direction in which the portable ultrasonic apparatus is inserted onto the shareable battery pack to limit a position of the portable ultrasonic apparatus with respect to the shareable battery pack.

7. The shareable battery pack according to claim 6, wherein, the housing is flat, the supporting surface and the first mounting part are arranged on a top wall of the housing, and the first mounting part and the first limiting portion are respectively arranged on opposite sides of the supporting surface.

8. The shareable battery pack according to claim 1, wherein the first mounting part comprises a first snap-in connector protruded and arranged on the housing for connecting with the portable ultrasonic apparatus in a buckled manner.

9. The shareable battery pack according to claim 8, wherein the first mounting part comprises two first snap-in connectors, a first unlocking member arranged between the two first snap-in connectors, first elastic members for driving the two first snap-in connectors to reset, and second elastic members for driving the first unlocking member to reset, wherein, the first elastic members are mounted in a line connecting the two first snap-in connectors and at opposite sides of the two first snap-in connectors, the first elastic members are configured to drive the two first snap-in connectors to approach each other, and the first unlocking member has a wide portion and a narrow portion, wherein the two first snap-in connectors are pressed against both sides of the wide portion by the first elastic members, the second elastic members are coupled to the first unlocking member to hold the wide portion of the first unlocking member between the two first snap-in connectors, the first unlocking member protrudes from the housing so that a position of the first unlocking member is changed to enable the two first snap-in connectors to abut on the narrow portion and change a distance between the two first snap-in connectors.

10. The shareable battery pack according to claim 9, wherein the two first snap-in connectors protrude from a top wall of the housing, and the first unlocking member protrudes from a side wall of the housing.

11. The shareable battery pack according to claim 1, further comprising at least one first magnetic socket comprising a first magnetic member for attracting at least one of the portable ultrasonic apparatus and the trolley, wherein the charging connector and the discharging connector are arranged in a same first magnetic socket or different first magnetic sockets to power the portable ultrasonic apparatus and charge the at least one battery.

12. The shareable battery pack according to claim 1, wherein, the second mounting part comprises a bayonet arranged on a side of the housing, and the bayonet is suitable to be fixed to a snap-in structure of the trolley.

13. A trolley for a portable ultrasonic apparatus, comprising:

a base; and a support table mounted on the base for supporting a shareable battery pack, wherein the support table comprises an installation part for bearing the shareable battery pack and a third mounting part detachably coupled to at least one of the shareable battery pack and the portable ultrasonic apparatus, wherein the shareable battery pack is capable of being installed on the installation part of the trolley, and when the shareable battery pack is detachably connected to the portable ultrasonic apparatus to form an integral unit, the integral unit is capable of being detachably mounted on the trolley through installation of the shareable battery pack on the installation part, with the shareable battery pack being on top of the trolley and the portable ultrasonic apparatus being on top of the shareable battery pack.

14. The trolley according to claim 13, further comprising:

a power supply having an output connector for docking with the shareable battery pack or the portable ultrasonic apparatus; and a control circuit connected with the power supply for controlling the power supply to supply power to the shareable battery pack or to supply power to the portable ultrasonic apparatus.

15. The trolley according to claim 13, further comprising a charging wire having an electrical input terminal and an electrical output terminal, wherein, the electrical output terminal is configured to electrically coupled to an external charging device, and the electrical input terminal is configured to dock with the shareable battery pack or the portable ultrasonic apparatus so as to conduct a current of the external charging device to the shareable battery pack or the portable ultrasonic apparatus.

16. The trolley according to claim 13, further comprising a power supply circuit for docking the shareable battery pack or the portable ultrasonic apparatus with an external charging device and controlling the external charging device to supply power to at least one of the shareable battery pack and the portable ultrasonic apparatus.

17. The trolley according to claim 13, wherein the installation part is on a top wall of the support table to enable the shareable battery pack to be detachably mounted on the top wall of the support table.

18. The trolley according to claim 14, further comprising at least one second magnetic socket provided with a second magnetic member for conveniently attracting at least one of the portable ultrasonic apparatus and the shareable battery pack, the output connector being arranged in the second magnetic socket for charging at least one of the portable ultrasonic apparatus and the shareable battery pack.

19. A power supply system for a portable ultrasonic apparatus, comprising:
   a trolley; and
   a shareable battery pack configured to supply power to the portable ultrasonic apparatus and comprises a first mounting part detachably coupled to the portable ultrasonic apparatus and a second mounting part detachably coupled to the trolley;
   wherein the trolley is configured to charge at least one of the shareable battery pack and the portable ultrasonic apparatus, and comprises a third mounting part detachably coupled to at least one of the shareable battery pack and the portable ultrasonic apparatus,
   wherein the shareable battery pack is capable of being installed on an installation part of the trolley, and when the shareable battery pack is detachably connected to the portable ultrasonic apparatus to form an integral unit, the integral unit is capable of being detachably mounted on the trolley through installation of the shareable battery pack on the installation part, with the shareable battery pack being on top of the trolley and the portable ultrasonic apparatus being on top of the shareable battery pack.

* * * * *